(12) United States Patent
Gaudin

(10) Patent No.: US 9,668,793 B2
(45) Date of Patent: Jun. 6, 2017

(54) ANATOMICALLY CUSTOMIZED PLANTAR BONE PLATE AND BONE PLATE SYSTEM

(75) Inventor: Bernd P. Gaudin, Berlin (DE)

(73) Assignee: Aristotech Industries GmbH, Luckenwalde (DE)

( * ) Notice: Subject to any disclaimer, the term of this patent is extended or adjusted under 35 U.S.C. 154(b) by 315 days.

(21) Appl. No.: 14/236,037

(22) PCT Filed: Aug. 24, 2012

(86) PCT No.: PCT/DE2012/100248
§ 371 (c)(1),
(2), (4) Date: Jan. 29, 2014

(87) PCT Pub. No.: WO2013/029600
PCT Pub. Date: Mar. 7, 2013

(65) Prior Publication Data
US 2014/0180343 A1  Jun. 26, 2014

(30) Foreign Application Priority Data
Aug. 31, 2011 (DE) .................... 20 2011 051 165 U

(51) Int. Cl.
*A61F 2/42* (2006.01)
*A61B 17/80* (2006.01)
*A61B 17/56* (2006.01)

(52) U.S. Cl.
CPC ........ *A61B 17/8061* (2013.01); *A61F 2/4225* (2013.01); *A61B 17/8057* (2013.01); *A61B 2017/568* (2013.01); *A61F 2002/4238* (2013.01)

(58) Field of Classification Search
CPC ........... A61F 2002/4238; A61F 2/4225; A61B 17/8061; A61B 17/8085
See application file for complete search history.

(56) References Cited

U.S. PATENT DOCUMENTS 2,662,988 A    12/1935  McKim
3,741,205 A     6/1973  Markolf et al.
(Continued)

FOREIGN PATENT DOCUMENTS

AT         406446      5/2000
DE        3113639      5/1982
(Continued)

OTHER PUBLICATIONS

International Search Report and Written Opinion for PCT/IB2014/001111, dated Sep. 8, 2014.
(Continued)

*Primary Examiner* — David Bates
(74) *Attorney, Agent, or Firm* — Andrus Intellectual Property Law, LLP

(57) ABSTRACT

An anatomically customized plantar bone plate and system for an angularly stable fixation for the arthrodesis of the tarsometatarsal I joint. The bone plate has a distal plate portion which extends in the longitudinal direction and in which a distal bore is formed for receiving a bone screw at a stable angle, a proximal plate portion which extends transverse to the longitudinal direction, and a central plate portion which extends between the distal and the proximal plate portions and which is made with a curved plate portion with at least one bending zone for the purpose of anatomical customization. A plantar bore for receiving a bone screw to be fixed to the sole of the foot at a stable angle and a bore that is medially inclined for receiving a bone screw to be fixed in a medially inclined manner at a stable angle are arranged in the proximal plate portion adjacently to each other transverse to the longitudinal direction.

7 Claims, 2 Drawing Sheets

(56) References Cited

U.S. PATENT DOCUMENTS

Figure 2:
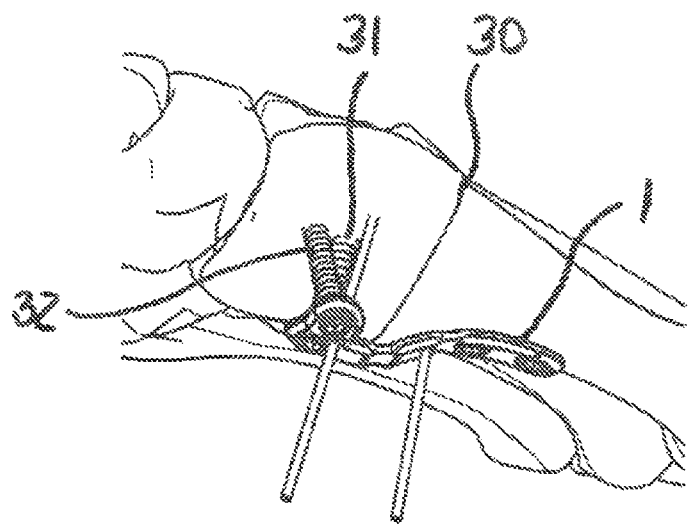

| | | |
|---|---|---|
| 3,757,591 A | 9/1973 | Taylor |
| 4,408,601 A | 10/1983 | Wenk |
| 4,454,876 A | 6/1984 | Mears |
| 4,616,634 A | 10/1986 | Vargas Garcia |
| 4,720,225 A | 1/1988 | Burt |
| 4,903,691 A | 2/1990 | Heinl |
| 4,959,065 A | 9/1990 | Arnett et al. |
| 5,529,075 A | 6/1996 | Clark |
| 6,129,728 A | 10/2000 | Schumacher et al. |
| 6,203,545 B1 | 3/2001 | Stoffella |
| 6,206,883 B1 | 3/2001 | Tunc |
| 6,306,140 B1 | 10/2001 | Siddiqui |
| 6,398,783 B1 | 6/2002 | Michelson |
| 6,423,068 B1 | 7/2002 | Reisberg et al. |
| 6,669,701 B2 | 12/2003 | Steiner et al. |
| 6,716,957 B2 | 4/2004 | Tunc |
| 6,719,759 B2 | 4/2004 | Wagner et al. |
| 6,730,091 B1 | 5/2004 | Pfefferle et al. |
| 6,886,799 B2 | 5/2005 | Yamanashi |
| 7,008,428 B2 | 3/2006 | Cachia et al. |
| 7,354,441 B2 | 4/2008 | Frigg |
| 7,468,069 B2 | 12/2008 | Baynham et al. |
| 7,655,029 B2 | 2/2010 | Niederberger et al. |
| 7,771,457 B2 | 8/2010 | Kay et al. |
| 7,976,570 B2 | 7/2011 | Wagner et al. |
| 8,118,846 B2 * | 2/2012 | Leither ............ A61B 17/8057 606/280 |
| 8,118,848 B2 | 2/2012 | Ducharme et al. |
| 8,246,661 B2 | 8/2012 | Beutter et al. |
| 8,632,545 B2 | 1/2014 | Sarangapani et al. |
| 2002/0045897 A1 | 4/2002 | Dixon et al. |
| 2002/0045901 A1 | 4/2002 | Wagner et al. |
| 2002/0183752 A1 | 12/2002 | Steiner et al. |
| 2003/0078668 A1 | 4/2003 | Michelson |
| 2004/0018228 A1 | 1/2004 | Fischell et al. |
| 2004/0034356 A1 | 2/2004 | LeHuec et al. |
| 2004/0073218 A1 | 4/2004 | Dahners |
| 2004/0102778 A1 | 5/2004 | Huebner et al. |
| 2004/0167522 A1 | 8/2004 | Niederberger et al. |
| 2004/0215192 A1 | 10/2004 | Justis et al. |
| 2004/0236332 A1 | 11/2004 | Frigg |
| 2005/0015092 A1 | 1/2005 | Rathbun et al. |
| 2005/0049594 A1 | 3/2005 | Wack et al. |
| 2005/0065521 A1 | 3/2005 | Steger et al. |
| 2005/0085818 A1 | 4/2005 | Huebner |
| 2005/0124994 A1 | 6/2005 | Berger et al. |
| 2005/0165400 A1 | 7/2005 | Fernandez |
| 2005/0165401 A1 | 7/2005 | Pack |
| 2005/0182408 A1 | 8/2005 | Pfefferle et al. |
| 2005/0192577 A1 | 9/2005 | Mosca et al. |
| 2005/0261688 A1 | 11/2005 | Grady, Jr. et al. |
| 2006/0015102 A1 | 1/2006 | Toullec et al. |
| 2006/0173458 A1 | 8/2006 | Forstein et al. |
| 2006/0235396 A1 | 10/2006 | Sanders et al. |
| 2006/0241607 A1 | 10/2006 | Myerson et al. |
| 2007/0016205 A1 | 1/2007 | Beutter et al. |
| 2007/0123885 A1 | 5/2007 | Kirschman |
| 2007/0233106 A1 | 10/2007 | Horan et al. |
| 2007/0276386 A1 | 11/2007 | Gerlach et al. |
| 2008/0051786 A1 | 2/2008 | Jensen |
| 2008/0132955 A1 | 6/2008 | Frigg |
| 2008/0300637 A1 | 12/2008 | Austin et al. |
| 2009/0024172 A1 | 1/2009 | Pizzicara |
| 2009/0210010 A1 | 8/2009 | Strnad et al. |
| 2010/0121325 A1 * | 5/2010 | Tyber ................ A61B 17/1717 606/62 |
| 2010/0256687 A1 | 10/2010 | Neufeld et al. |
| 2011/0295325 A1 | 12/2011 | Wagner et al. |
| 2012/0265254 A1 | 10/2012 | Horan et al. |
| 2013/0190829 A1 | 7/2013 | Batsch et al. |

FOREIGN PATENT DOCUMENTS

| | | |
|---|---|---|
| DE | 102005044841 | 3/2006 |
| DE | 102006000948 | 10/2006 |
| DE | 102005042766 | 1/2007 |
| DE | 102005043285 | 1/2007 |
| DE | 69835968 | 5/2007 |
| DE | 102009020285 A1 | 11/2010 |
| DE | 102010025001 | 12/2011 |
| EP | 0243114 | 10/1987 |
| EP | 1158916 | 7/2004 |
| EP | 1158915 | 9/2004 |
| EP | 1468655 | 10/2004 |
| EP | 1255498 | 11/2005 |
| EP | 1897509 A1 * | 9/2006 |
| EP | 1897509 A1 | 3/2008 |
| EP | 1702577 | 11/2008 |
| EP | 2016918 | 1/2009 |
| EP | 1677693 | 4/2009 |
| FR | 2667913 | 4/1992 |
| FR | 2739151 | 3/1997 |
| FR | 2886535 | 12/2006 |
| WO | 9709000 | 3/1997 |
| WO | 9829058 | 7/1998 |
| WO | 0053110 | 9/2000 |
| WO | 0154601 | 8/2001 |
| WO | 02096309 | 12/2002 |
| WO | 2005041796 | 5/2005 |
| WO | 2005053111 | 6/2005 |
| WO | 2006014436 | 2/2006 |
| WO | 2007025520 | 3/2007 |
| WO | 2010059497 A1 | 5/2010 |
| WO | 2011163092 | 12/2011 |
| WO | 2012000627 | 1/2012 |

OTHER PUBLICATIONS

Myerson, Mark, M.D., "Correction of Hallux Valgus Deformity with the Ludloff Osteotomy Surgical Technique", Joint Meeting of American Orthopedic Foot & Ankle Society and the Japanese Surgery Society for the Foot, Nov. 13-15, 1997, Waikoloa, HI.

International Search Report for PCT/DE2012/100248 dated Dec. 20, 2012.

International Search Report for PCT/DE2010/075167, mailed Apr. 15, 2011.

Acevedo, Jorge I, Sammarco, V. James, Boucher, Henry R., Parks, Bert G., Schon, Lew C., Myerson, Mark S; Mechanical Comparison of Cyclic Loading in Five Different First Metatarsal Shaft Osteotomies; Foot & Ankle International, Aug. 2002; vol. 23, No. 8, pp. 711-716.

Cisar, J., Holz, U, Jenninger, w., Uhlig. Chr.; Die Osteotomie nach Ludloff bei der Hallux-valgus-Operation; Aktuelle Traumatol. 13; 1983; pp. 247-249.

Hyer, Christopher F., Glover, Jason P., Berlet, Gregory C., Philbin, Terrence, M, Lee, Thomas H.; A Comparison of the Crescentic and Mau Osteotomies for Correction of Hallux Valgus; Journal of Foot and Ankle Surgery; Mar./Apr. 2008; vol. 47, No. 2,; pp. 103-111.

Ludloff, Prof. Dr. K.; Die Beseitigung des Hallux valgus durch die schrage planta-dorsale Osteotomie des Metatarus I.; Arch. Klin. Chir.; 110:364-387; 1918.

Mau, C., Lauber, H.J.; Die operative Behandlung des Hallux valgus (Nachuntersuchungen); 1926, 197:361-377.

Sammarco, V. James; Surgical Strategies: Mau Osteotomy for Correction of Moderate and Severe Hallux Valgus Deformity; Foot & Ankle International; Jul. 2007; 28(7); pp. 857-864.

Saxena, Amol, McCammon, Derek; The Ludloff Osteotomy: A Critical Analysis; Journal of Foot and Ankle Surgery; 1997; vol. 36, No. 2, pp. 100-105.

Trnka, H.-J., Hofstaetter, S.G., Hofstaetter, J.G., Gruber, F., Adams Jr., S.B., Easley, M.E.; Intermediate-Term Results of the Ludloff Osteotomy in One Hundred and Eleven Feet; The Journal of Bone and Joint Surgery; Mar. 2008; vol. 90-A(3); pp. 531-539.

International Search Report for PCT/2006/001508, mailed Feb. 8, 2007.

(56) References Cited

OTHER PUBLICATIONS

"Orthopaedic Product News", Aug. 2005, Retrieved from the Internet: URL:http://www.orthoworld.com/us_opn-2005-08.pdf [retrieved on May 26, 2009], p. 30, Hallux Valgus Correction with a Low Profile Locking Plate.
Iselin, Lukas D. et al., Operative Management of Common Forefoot Deformities a Representative Survey of Australian Orthopaedic Surgeons, Foot & Ankle Specialist, vol. X/ No. X, 1-7 (2012).
Miller, Michael J., DMP et al., Inverted Z-scarf Osteotomy for Hallux Valgus Deformity Correction: Intermediate-term Results in 55 Patients, The Journal of Foot and Ankle Surgery, 50: 55-61 (2011).
Dereymaeker, Greta, MD, PhD, Scarf Osteotomy for Correction of Hallux Valgus—Surgical Technique and Results as Compared to Distal Cheveron Osteotomy, The Hallux, vol. 5/ No. 3, 513-523 (Sep. 2000).
Steck, Jerome K., DPM, Long Z-Osteotomy: A Review and New Modification to Correct Troughing, The Journal of Foot and Ankle Surgery, vol. 40/ No. 5, 305-310 (Sep./Oct. 2001).
Adam, Stephanie P., Do et al., Outcomes after Scarf Osteotomy for Treatment of Adult Hallux Valgus Deformity, Clinical Orthopaedics and Related Research, 469: 854-859 (2011).
Trnka, Hans-Jorg, MD et al., Six First Metatarsal Shaft Osteotomies—Mechanical and Immobilization Comparisons, Clinical Orthopaedics and Related Research, No. 381, 256-265 (Mar. 10, 2000).
Aminian, Arash, M.D. et al., Scarf Osteotomy for Hallux Valgus Deformity: An Intermediate Followup of Clinical and Radiographic Outcomes, Foot & Ankle International, vol. 27/ No. 11, 883-886 (Nov. 2006).

Weil, Lowell Scott, DPM, Scarf Osteotomy for Correction of Hallux Valgus—Historical Perspective, Surgical Technique, and Results, The Hallux, vol. 5/ No. 3, 559-580 (Sep. 2000).
Vienne, Patrick, M.D. et al, Comparative Mechanical Testing of Different Geometric Designs of Distal First Metatarsal Osteotomies, Foot & Ankle International, vol. 28/ No. 2, 232-236 (Feb. 2007).
Lipscombe, Stephen, MRCS et al, Scarf Osteotomy for the Correction of Hallux Valugs: Midterm Clinical Outcome, The Journal of Food and Ankle Surgery, vol. 47/ No. 4, 273-277 ( Jul./Aug. 2008).
Barouk, Louis Samuel, MD, Scarf Osteotomy for Hallux Valgus Correction—Local Anatomy, Surgical Technique, and Combination with Other Forefoot Procedures, The Hallux, vol. 5/ No. 3, 525-557 (Sep. 2000).
Crevoisier, Xavier et al., The Scarf Osteotomy for the Treatment of Hallux Valgus Deformity: A Review of 84 Cases, Foot & Ankle International, vol. 22/ No. 12, 970-976 (Dec. 2001).
Coetzee, J. Chris, M.D., Scarf Osteotomy for Hallux Valgus Repair: The Dark Side, Foot & Ankle International, vol. 24/ No. 1, 29-33 (Jan. 2003).
Interventional Procedures Programme—Interventional procedure overview of surgical correction of hallux valgus using minimal access techniques, National Institute for Health and Clinical Excellence, p. 1, 9.
Comparison of Preoperative to Postoperative Measurement at 6 Weeks, 1 and 2 Years Postoperative, Table 1.
O'Briain, David E. et al., Use of a Geometric Formula to Improve the Radiographic Correction Achieved by the Scarf Osteotomy, Foot & Ankle International, vol. 33/ No. 8, 647-654 (Aug. 2012).
Easley, Mark E., M.D., et al., Current Concepts Review: Hallux Valgus Part II: Operative Treatment, Foot & Ankle International, vol. 28/ No. 6, 748-758 (Jun. 2007).
Partial International Search Report for PCT/IB2014/001111 dated Sep. 16, 2014.

* cited by examiner

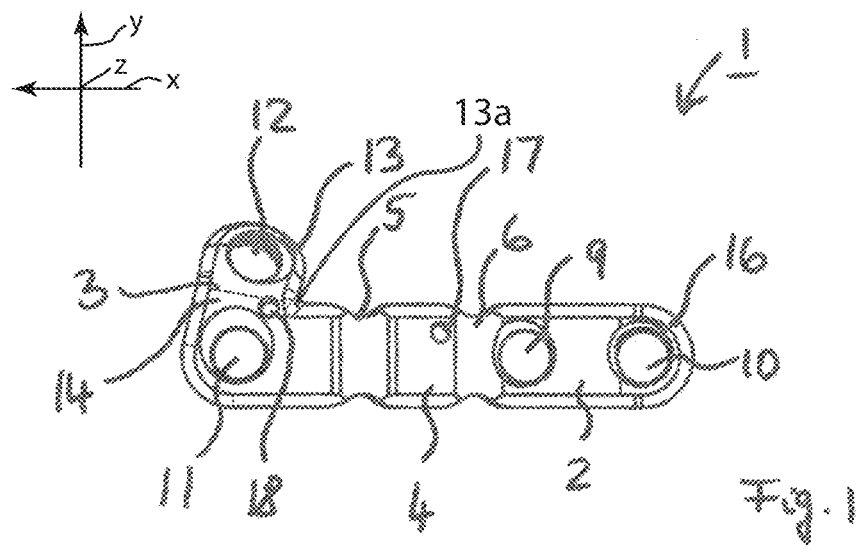
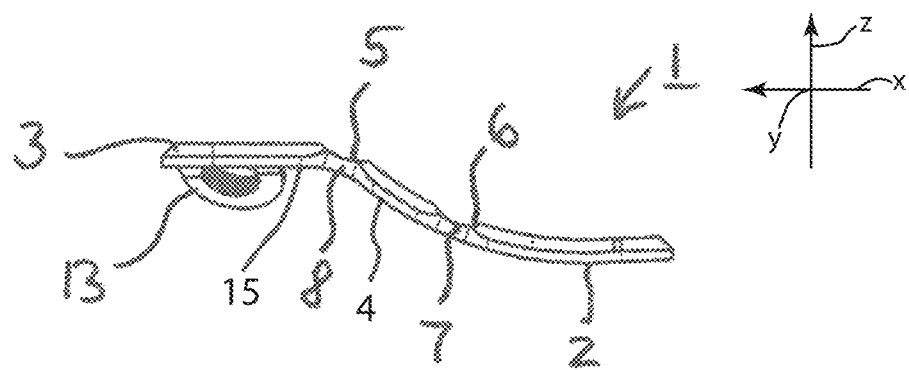

ANATOMICALLY CUSTOMIZED PLANTAR BONE PLATE AND BONE PLATE SYSTEM

CROSS-REFERENCE TO RELATED APPLICATIONS

This application is the U.S. national stage application of International Application PCT/DE2012/100248, filed Aug. 24, 2012, which international application was published on Mar. 7, 2013, as International Publication WO2013/029600 in the English language. The International Application claims priority of German Patent Application 20 2011 051 165.0, filed Aug. 31, 2011. The international application and German patent application are fully incorporated herein by reference.

FIELD OF THE INVENTION

The invention relates to an anatomically customised plantar bone plate for fixation for the arthrodesis of the tarsometatarsal I joint, and also to a bone plate system.

BACKGROUND OF THE INVENTION

Such bone plates serve for fixation of the tarsometatarsal I joint in the context of stiffening of a joint. The objective is mechanical stabilisation of the bone parts relative to one another, which makes it possible for a patient to put weight on the foot again for example very quickly after an operation. Known bone plates for arthrodesis of the tarsometatarsal I joint have a plurality of bores, into each of which a bone screw can be screwed at a stable angle.

In the document WO 2010/059497 A1 a dorsal bone plate is disclosed for angularly stable fixation for the arthrodesis of the tarsometatarsal I joint. Into proximal plate portion of the bone plate a group of three bores is formed, each of these bores serving to receive a bone screw at a stable angle. Also the distal plate portion of the bone plate is provided with three bores to receive bone screws in an angularly stable manner. Furthermore a longitudinal slot is provided in the distal plate portion to receive a further bone screw at a flexible angle. In one embodiment, a bend can be provided in the region between the proximal and the distal plate portions. The dorsal positioning of the bone plate has the disadvantage that it results in only a limited soft tissue covering on the foot. A high bending load also occurs for the bone plate. When the foot is loaded the tarsometatarsal I joint gap may open up.

The document DE 10 2009 020 285 A1 discloses a bone plate which is of substantially L-shaped or T-shaped construction for fixing bone parts in surgical corrections of Hallux Valgus deformity. The branches of the L or T have through bores to receive the heads of bone screws.

In the document EP 1 897 509 B1 a bone plate is disclosed which has a plurality of openings to receive one or more bone screws.

The document US 2006/0015102 A1 discloses a bone plate for osteosynthesis of bone fragments. Thus the bone plate has a longitudinal slot and a plurality of bores.

Also in the document US 2010/0256687 A1 a bone plate is described in which at each end an end portion extends obliquely with respect to the longitudinal axis of the bone plate. Openings for bone screws are produced both in the central region and also in the angled end portions.

The document WO 2010/059497 A1 discloses a bone plate with a longitudinal slot and several further through bores to receive screws, in particular bone screws.

BRIEF SUMMARY OF THE INVENTION

The object of the invention is to provide improved technologies in conjunction with a bone plate for angularly stable fixation for the arthrodesis of the tarsometatarsal I joint, with which an optimised mechanical stabilisation of the stiffening of a joint is possible. Furthermore the implantability of the bone plate should be simplified.

This object is achieved according to the invention by an anatomically customised plantar bone plate for angularly stable fixation for the arthrodesis of the tarsometatarsal I joint according to the independent claim 1. Furthermore a bone plate system for the arthrodesis of the tarsometatarsal I joint is provided. Advantageous embodiments of the invention are the subject matter of dependent subordinate claims.

The invention refers to the concept of an anatomically customised or adapted plantar bone plate for angularly stable fixation for the arthrodesis of the tarsometatarsal I joint comprising a distal plate portion which extends in the longitudinal direction and in which a distal bore (opening) is formed to receive a bone screw at a stable angle, a proximal plate portion which extends transversely with respect to the longitudinal direction, and a central plate portion which extends between the distal and the proximal plate portions and for the anatomical customisation is formed with a bent plate portion, wherein a plantar bore (opening) to receive a bone screw to be fixed at a stable angle to the sole of the foot and a medially inclined bore to receive at a stable angle a bone screw to be fixed so as to be angled in the medial direction are disposed adjacent to one another in the proximal plate portion transversely with respect to the longitudinal direction.

According to the invention a bone plate system for the arthrodesis of the tarsometatarsal I joint is provided with an anatomically customised or adapted plantar bone plate, wherein a distal plate portion which extends in the longitudinal direction and in which a distal bore is drilled to receive a bone screw in an angularly stable manner, a proximal plate portion which extends transversely with respect to the longitudinal direction, and a central plate portion which extends between the distal and the proximal plate portions and for the anatomical customisation is designed with a bent plate portion, wherein a plantar bore to receive a bone screw to be fixed to the sole of the foot at a stable angle and a bore angled in the medial direction to receive at a stable angle a bone screw to be fixed so as to be angled in the medial direction are disposed adjacent to one another in the proximal plate portion transversely with respect to the longitudinal direction.

The proposed plantar bone plate assists the stability of the stiffening of a joint effected surgically by means of the bone plate, in that said bone plate can be fixed in the proximal plate region by means of bone screws disposed adjacent to one another, of which one bone screw is to be fixed to the sole of the foot and another bone screw is to be fixed medially on the bone. In this way not only are the plantarly more favourable force ratios on the tarsometatarsal I joint used, but in addition a medial fixation component of the bone plate is made possible. As a result the mechanical stability of the angularly stable fixation on the bone is improved.

Furthermore it is advantageous that during implantation of the bone plate said plate can be fixed initially from the medial area, in order then to screw the further bone screws into the plantar region which is more difficult to access. As a result, precisely positioned fixing of the bone plate relative to the joint to be stiffened is made easier for the surgeon.

This makes it possible, in spite of the sometimes more difficult implantation, to use the conditions of the action of force on the bone plate which are more advantageous for the plantar area, as a precisely located fixation with sufficient mechanical stability is enabled with the aid of the proposed anatomically customised plantar bone plate.

The fixation of the bone screws at a stable angle in the respective associated bore can be performed in various ways. Different embodiments are known per se. For example, the bore is provided with a threaded portion into which a matching thread on the screw head is turned as the bone screw is screwed in, so that in the screwed-in state of the bone screw an angular stability is ensured.

The central plate portion is preferably free from screw bores, in particular in the bent plate portion. The mechanical stability of the bone plate is further assisted in this way.

In one embodiment it may be provided that the periphery of the bone plate is chamfered or rounded in order to avoid disadvantageous effects on the surrounding tissue in the body.

The anatomically customised design of the plantar bone plate means that the bone plate is preformed during production, so that after production the bone plate has a shape customised to the anatomical conditions in the region of the tarsometatarsal I joint.

A preferred embodiment of the invention provides that the bore angled in the medial direction is formed on a laterally projecting portion of the proximal plate portion. The laterally projecting portion of the bone plate can be formed for example with a lateral bracket. In the configuration in which the laterally projecting portion is formed on the proximal plate portion the bone plate is preferably L-shaped.

In an advantageous embodiment of the invention it may be provided that the laterally projecting portion is inclined towards the underside of the plate relative to a central portion of the proximal plate portion. In this case, when viewed in the longitudinal direction, the lateral portion is bent round or angled towards the underside relative to the central portion in the region of the proximal plate portion.

An advantageous embodiment of the invention provides that the laterally projecting portion is provided with an offset. Such an offset is comparable to the offsets of saw-teeth. The offset is preferably formed with an offset angle of approximately 3 to approximately 10 degrees. In a preferred embodiment a corner region of the laterally projecting portion is offset, said corner region being disposed on the side of the laterally projecting portion facing the distal plate portion.

In a further development of the invention, the central plate portion preferably has a proximal bending zone which is associated with the joint gap of the joint to be fixed. The proximal bending zone or bend may be configured in such a way that the proximal bending zone adjoins a substantially flat plate portion which begins in the region of the proximal plate portion and extends to the central plate portion. The proximal bend then leads into the central plate portion, which may be flat or, when viewed from the side towards the bone plate, may be bent. In one embodiment the central plate portion is then coupled via a further bending zone or bend to the distal plate portion, which in this or other embodiments may be designed as a flat plate portion or, when viewed from the side towards the bone plate, as bent plate portion. The one or the several bending zones or bends enable an optimised customisation of the shape of the bone plate to the anatomical conditions.

In an advantageous embodiment of the invention it may be provided that one or more bending zones are formed in the central plate portion in each case with a thinning of the material. The thinning of the material forms waists which can be used before the actual implantation if desired for additional customisation of the shape of the bone plate to anatomical conditions, as bends predetermined during production are modified, manually or by the use of a tool.

In an advantageous embodiment of the invention it may be provided that, viewed from the side, an S-shaped plate contour is formed by means of the distal and the proximal plate portions and of the central plate portion extending therebetween.

A preferred modification of the invention provides that the plantar bore and the bore angled in the medial direction are formed with screwing axes which cross on the underside of the plate for the bone screw to be fixed to the sole of the foot and angled in the medial direction. The crossing of the screwing axes, which are predetermined for example by means of a threaded portion in the bore, is visible in particular in a transverse viewing direction with respect to the longitudinal direction. The resistance to pulling off of the plate is significantly increased by means of crossovers of the screwing axes. Pull-out forces increase, since not only does the thread constitute an anchor, but also the crossing screws serve as bolts.

In an advantageous embodiment of the invention it may be provided that in the distal plate portion a further distal bore is formed in the longitudinal direction adjacent to the distal bore to receive a further bone screw at a stable angle. Like the bone screw for the distal bore, the further bone screw for the further distal bore should also be screwed into the sole of the foot during the fixing of the bone plate at a stable angle.

An advantageous embodiment of the invention provides one or more openings to receive a Kirschner wire at a stable angle. Such wires are also known as K-wires. In surgery they serve as an aid, for example for provisional position fixing.

A further development of the invention preferably provides that an insertion axis of an opening which is formed in the proximal plate portion or adjacent thereto extends substantially parallel to the screwing axis for the plantar bone screw in the plantar bore. The insertion axis corresponds to the axis of the bore with which the opening was formed. The Kirschner wire is guided along this axis in the opening as it is inserted or introduced into the opening. It may be provided that in addition or alternatively an insertion axis of a further opening formed in the distal plate portion or adjacent thereto is formed with its axis substantially parallel to the screwing axis of the bone screw to be screwed into the proximal bore to the sole of the foot. With the aid of the parallelism of the axes it is possible for the surgeon in each case first of all to introduce a K-wire into the corresponding bore and thus to have an orientation for the screwing direction of the associated bone screw. The required parallelism between the provisionally introduced K-wire and the screwed-in bone screw can also be checked later on X-ray images.

With the aid of the proposed bone plate and also of the bone plate system for arthrodesis of the tarsometatarsal I joint, a method for implantation of the bone plate is made possible, wherein the anatomically customised, plantar bone plate is introduced into an associated body orifice and is disposed in the region of the tarsometatarsal I joint, the bone plate is (provisionally) fixed by screwing an associated bone screw into the bore which is angled in the medial direction, and then further bone screws are screwed into the proximal bore as well as the plantar bore, so that all the bone screws are received at a stable angle in the respective associated bore. It may be provided that a tension screw is additionally screwed in dorsally into the bone parts of the joint which are fixed by means of the bone plate. With the aid of this method it is possible for the surgeon to position and to secure the bone plate which is to be fixed initially by means of the bone plate which is angled in the medial direction, that is to say by means of the introduction of a bone screw into a region which is more readily accessible during surgery, namely the medial central foot region. Then the further bone screws can be screwed in to the sole of the foot. The method preferably provides for the arrangement of proximal bending plate portion which is bent for the anatomical customisation adjacent to the (former) joint gap.

DESCRIPTION OF PREFERRED EMBODIMENTS OF THE INVENTION

Figure 4:
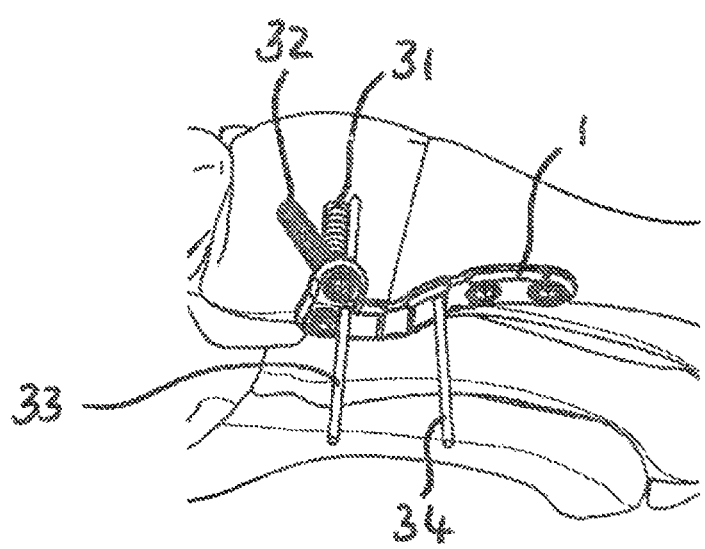
Figure 5:
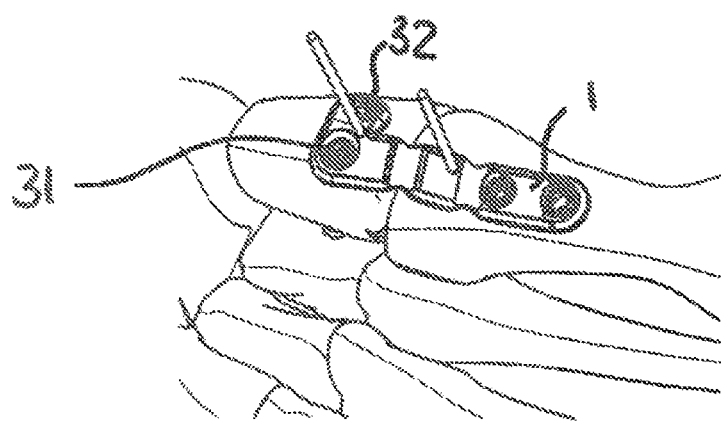

The invention is explained below in greater detail on the basis of preferred embodiments with reference to the drawings. In the drawings:

FIG. 1 shows in plan view an anatomically customised plantar bone plate for fixation at a stable angle for arthrodesis of the tarsometatarsal I joint, FIG. 2 shows the bone plate according to FIG. 1 in a front side view, FIG. 3 shows a schematic representation of a portion of a foot skeleton wherein the bone plate according to FIG. 1 and FIG. 2 is fixed at a stable angle on the tarsometatarsal I joint, FIG. 4 shows a schematic representation of the portion of the foot skeleton according to FIG. 3 from a further perspective, and FIG. 5 shows a schematic representation of the portion of the foot skeleton according to FIG. 3 from a further perspective.

FIG. 1 shows an anatomically customised plantar bone plate 1 contoured relative to longitudinally extending x, laterally extending y and vertically extending z axes lying perpendicular to each other which bone plate 1 is formed by a distal plate portion 2 and a proximal plate portion 3. A central plate portion 4, which according to FIG. 2 is provided in the region of material waists 5, 6 with a distal bending zone 7 as well as a proximal bending zone 8, is disposed between the distal plate portion 2 and the proximal plate portion 3, so that when viewed from the side the bone plate is formed with an S shape or S contour. The S contour is part of the anatomical adaptation of the bone plate 1.

According to FIG. 1 a distal bore 9 as well as a further distal bore 10 are disposed adjacent to one another in the distal plate portion 2 in the longitudinal direction of the distal plate portion 2 along the x axis. The distal bore 9 and the further distal bore 10 both serve to receive an associated bone screw at a stable angle, which is also shown at the bottom in FIGS. 3 to 5.

In a comparable manner, associated bone screws are received at a stable angle in the proximal plate portion 3 a plantar bore 11 as well as a bore 12 angled in the medial direction, which is likewise shown at the bottom in the FIGS. 3 to 5. As can best be seen from FIG. 2, a bracket 13 is provided in the region of the proximal plate portion 3 with the bore 12 which is angled in the medial direction and by comparison with an adjacent portion 14 in the proximal plate portion 3 is angled relative to the underside 15 of the bone plate 1 and the y and z axes. Furthermore the bracket 13 is offset at 13a, namely at an angle of approximately 5 degrees. The three-dimensional embodiment of the proximal plate portion 3 forms a further measure for anatomical customisation of the bone plate 1 to the anatomical situation in the region of the tarsometatarsal I joint. The described features of the anatomical customisation of the bone plate 1 are already formed during the production of the bone plate 1. An additional customisation or correction of the shape of the bone plate 1 may be undertaken by the user directly before the implantation, wherein in particular the bending zones 7, 8 are used in the region of the inwardly extending material waists 5, 6 formed on the outer periphery of the central plate portion 4.

According to the representations in FIGS. 1 and 2, the bone plate 1 is provided with a peripheral chamfer or rounding 16.

In the central plate portion 4 and in the proximal plate portion 3 the bone plate 1 has respective openings 17, 18. The openings 17, 18 serve to receive a respective Kirschner wire, which is shown at the bottom in FIGS. 3 and 5. The Kirschner wires can be used by the surgeon as an and during the implantation of the bone plate 1.

FIGS. 3 to 5 show perspective representations of a region of a foot skeleton with a tarsometatarsal I joint 30, which for stiffening is secured by means of the bone plate 1 according to FIGS. 1 and 2. For this purpose after the fixing of the bone plate 1 a respective bone screw (not shown) is screwed in at a stable angle in the distal bore 9 and the further distal bore 10. In this case the angular stability of the screwed-in bone screws is achieved in that a conical thread on the respective screw head engages in a matching thread in the distal bore 9 and the further distal bore 10. The bone screws in the distal plate portion 2 are screwed in divergently.

Also a respective bone screw 31, 32 is screwed into the plantar bore 11 and the bore 12 angled in the medial direction, wherein the two bone screws 31, 32 cross in the bone according to the representations in FIGS. 3 and 4.

FIGS. 3 and 4 also show that Kirschner wires 33, 34 which are introduced into the openings extend in each case with their axis parallel to one of the bone screws.

The features of the invention disclosed in the foregoing description, the claims and the drawings may be significant, both individually and in any combination, for the implementation of the invention in its different embodiments.

The invention claimed is:

1. An anatomically customised plantar bone plate contoured relative to longitudinally extending x, laterally extending y and vertically extending z axes lying perpendicular to each other for angularly stable fixation for the arthrodesis of the tarsometatarsal I joint, the bone plate comprising:
   a distal plate portion which defines a first outer free end through which the x axis passes and which extends entirely in a longitudinal direction relative to the x axis, and in which a distal bore is formed and adapted to receive a bone screw at a stable angle,
   a proximal plate portion which defines a second outer free end through which the x axis passes and which extends transversely with respect to the longitudinal direction along the y axis and includes a laterally projecting portion being formed with an angled offset edge extending in a direction from one of longitudinally extending opposite side edges of the proximal plate portion toward the distal plate portion when viewed in a xy plane defined by the x and y axes, and
   a central plate portion which extends between the distal and the proximal plate portions and is formed with a bent plate portion with at least one bending zone configured to be bent during installation of the bone plate, wherein a plantar bore in the proximal plate portion adapted to receive a bone screw to be fixed at a stable angle to the sole of the foot and a medial bore in the laterally projecting portion angled in a medial direction and adapted to receive at a stable angle a bone screw to be fixed so as to be angled in the medial direction are disposed adjacent to one another in the proximal plate portion and define screwing axes which cross on an underside of the bone plate and are angled in the medial direction, wherein the distal bore and the plantar bore define screwing axes which are parallel to the z axis, wherein the least at one bending zone in the central plate portion is defined by two bending zones formed with a thinning of material in inwardly-extending waists formed on an outer periphery of the central plate portion on longitudinally extending opposite side edges thereof between the distal bore and the plantar bore when viewed in the xy plane, such that material between the proximal plate portion and one side edge of the central plate portion, and between the distal plate portion and an opposite side edge of the central plate portion is reduced in thickness relative to thickness of the central plate portion when viewed in a xz plane defined by the x and z axes, wherein, when viewed in the xz plane, an S-shaped plate contour is formed by the distal and proximal plate portions and the central plate portion extending therebetween, wherein, in the distal plate portion in the longitudinal direction adjacent to the distal bore, a further distal bore is formed and adapted to receive a further bone screw at a stable angle, wherein, when viewed in the xy plane, the bone plate has an L-shaped contour, wherein the distal bore is located between the one side of the central plate portion and the first outer free end, the plantar bore is located between the opposite side of the central plate portion and the second outer free end and the further distal bore is located between the distal bore and the first outer free end, wherein the distal bore, the plantar bore, the further distal bore, and the first and second outer free ends are aligned along the x axis when viewed in the xy plane, and wherein the medial bore is located outside the one of the opposite side edges of the proximal plate portion.

2. A bone plate as claimed in claim 1, wherein the laterally projecting portion is bent towards an underside of the plate with respect to a central portion of the proximal plate portion and the y and z axes.

3. A bone plate as claimed in claim 1, wherein the offset edge in the laterally projecting portion extends at an angle in the range of 3-10° relative to the y axis.

4. A bone plate as claimed in claim 1, wherein the at least one bending zone in the central plate portion includes a proximal bending zone which is adapted to be applied to a joint gap of a joint to be fixed.

5. A bone plate as claimed in claim 1, further comprising one or more openings adapted to receive a Kirschner wire at a stable angle.

6. A bone plate as claimed in claim 5, wherein an insertion axis of one of the openings which is formed in the proximal plate portion or adjacent thereto extends substantially parallel to the screwing axis of the plantar bore.

7. A bone plate system for arthrodesis of the tarsometatarsal I joint, the bone plate system comprising:

an anatomically customised plantar bone plate contoured relative to longitudinally extending x, laterally extending y and vertically extending z axes lying perpendicular to each other, in which a distal plate portion defines a first outer free end through which the x axis passes and which extends entirely in a longitudinal direction relative to the x axis and in which a distal bore is formed, a proximal plate portion which defines a second outer free end through which the x axis passes and which extends transversely with respect to the longitudinal direction along the y axis and includes a laterally projecting portion being formed with an angled offset edge extending in a direction from one of longitudinally extending opposite side edges of the proximal plate portion toward the distal plate portion when viewed in a xy plane defined by the x and y axes, and a central plate portion which extends between the distal and the proximal plate portions and is formed with a bent plate portion with at least one bending zone configured to be bent during installation of the bone plate, wherein a plantar bore in the proximal plate portion and a medial bore in the laterally projecting portion angled in a medial direction are disposed adjacent to one another in the proximal plate portion and define screwing axes which cross on an underside of the bone plate and are angled in the medial direction, and a plurality of bone screws screwed at a stable angle into the distal bore, the plantar bore and the medial bore, wherein the distal bore and the plantar bore define screwing axes which are parallel to the z axis, wherein the at least one bending zone in the central plate portion is defined by two bending zones formed with a thinning of material in inwardly-extending waists formed on an outer periphery of the central plate portion on longitudinally extending opposite side edges thereof between the distal bore and the plantar bore when viewed in the xy plane, such that material between the proximal plate portion and one side edge of the central plate portion, and between the distal plate portion and an opposite side edge of the central plate portion is reduced in thickness relative to thickness of the central plate portion when viewed in a xz plane defined by the x and z axes, wherein, when viewed in the xz plane, an S-shaped plate contour is formed by the distal and proximal plate portions and the central plate portion extending therebetween, wherein, in the distal plate portion in the longitudinal direction adjacent to the distal bore, a further distal bore is formed and adapted to receive a further bone screw at a stable angle, wherein, when viewed in the xy plane, the bone plate has an L-shaped contour, wherein the distal bore is located between the one side of the central plate portion and the first outer free end, the plantar bore is located between the opposite side of the central plate portion and the second outer free end and the further distal bore is located between the distal bore and the first outer free end, wherein the distal bore, the plantar bore, the further distal bore, and the first and second outer free ends are aligned along the x axis when viewed in the xy plane, and wherein the medial bore is located outside the one of the opposite side edges of the proximal plate portion.

* * * * *